United States Patent [19]

Cesa et al.

[11] Patent Number: 4,705,864
[45] Date of Patent: Nov. 10, 1987

[54] ARYL OXIME DERIVATIVES OF HYDANTOINS

[75] Inventors: Mark C. Cesa, South Euclid; James E. Rinz, University Heights; Teodora T. Kopp, Garfield Heights, all of Ohio

[73] Assignee: The Standard Oil Company, Cleveland, Ohio

[21] Appl. No.: 928,770

[22] Filed: Nov. 10, 1986

[51] Int. Cl.$^4$ ............... C07D 403/04; C07D 233/76; C07D 233/78
[52] U.S. Cl. .................. 548/309; 548/311; 548/312; 548/314
[58] Field of Search ............ 548/314, 309, 311, 312

[56] References Cited

U.S. PATENT DOCUMENTS 3,671,540  6/1972  Schocke et al. ............ 548/314

Primary Examiner—Richard A. Schwartz
Attorney, Agent, or Firm—Charles S. Lynch; John E. Miller; Larry W. Evans

[57] ABSTRACT

A compound of the formula

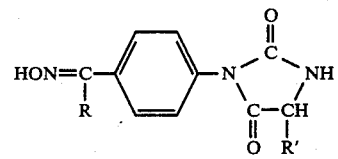

useful as an ultraviolet light absorber where each of R and R' has zero to 10 C atoms and no ethylenic or acetylenic unsaturation; R is H or hydrocarbyl; R' is H, hydrocarbyl, or hydrocarbyl substituted with hydrocarbylcarbonylamino, dithydrocarbylcarbonyl)amino, hydrocarbylcarbonyl(hydrocarbyl)amino, formylamino, diformylamino and formyl(hydrocarbyl)amino, hydrocarbyloxy, hydrocarbylthio, formylthio, hydrocarbylcarbonylthio, hydrocarbyloxycarbonyl, hydrocarbyl carboxyl, hydrocarbylamino, dihydrocarbylamino, formyl, 3-indolyl, 3-(1-hydrocarbyl)indolyl, 3-(1-hydrocarbylcarbonyl)indolyl, 3-(1-formyl)indolyl, carbamoyl, hydrocarbylcarbamoyl, dihydrocarbylcarbamoyl, 5-imidazolyl, 5-(3-hydrocarbyl)imidazolyl, 5-(3-hydrocarbylcarbonyl)imidazolyl, or 5-(3-formyl)imidazolyl.

2 Claims, No Drawings

ARYL OXIME DERIVATIVES OF HYDANTOINS

This invention relates to new compounds of the formula,

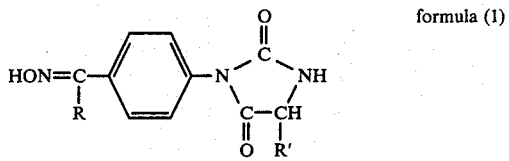

formula (1)

where each of R and R' has zero to 10 C atoms and no ethylenic or acetylenic unsaturation; R is H or hydrocarbyl; R' is H, hydrocarbyl, or hydrocarbyl substituted with hydrocarbylcarbonylamino, di(hydrocarbylcarbonyl)amino, hydrocarbylcarbonyl(hydrocarbyl)amino, formylamino, diformylamino and formyl(hydrocarbyl)amino, hydrocarbyloxy, hydrocarbylthio, formylthio, hydrocarbylcarbonylthio, hydrocarbyloxycarbonyl, hydrocarbyl carboxyl, hydrocarbylamino, dihydrocarbylamino, formyl, 3-indolyl, 3-(1-hydrocarbyl)indolyl, 3-(1-hydrocarbylcarbonyl)indolyl, 3-(1-formyl)indolyl, carbamoyl, hydrocarbylcarbamoyl, dihydrocarbylcarbamoyl, 5-imidazolyl, 5-(3-hydrocarbyl)imidazolyl, 5-(3-hydrocarbylcarbonyl)imidazolyl, or 5-(3-formyl)imidazolyl. Usually R contains 0 to 6 C atoms.

These compounds are useful ultraviolet light absorbers. They can be used in plastic compositions to impart this property. It is believed that the excellent UV light absorption of these compounds may be related to the fact that the compounds of the invention have the oxime, arene and hydantoin chromophores in conjugation. Such structures are believed to be novel.

The compounds of the invention all have high molar extinction coefficients, $\lambda_{max}=250\text{–}290$ nm, $\epsilon \geq 10^4$. In our work the particular solvent used in measuring the absorbance to determine the extinction coefficients was methanol.

The products of the present invention where R is H can be prepared by reacting the compound

Formula (2)

where R" is phenyl or a $C_1$ to $C_6$ alkyl group, with the acetal of 4-aminobenzaldehyde derived from a $C_1$ to $C_6$ monoalkanol or a $C_1$ to $C_6$ alkanediol, said reaction being carried out in a solvent such as dioxane, THF, diethyl ether, glymes and di-n-butyl ether in the presence of a sterically hindered base, and then reacting the product of such reaction with hydroxylamine hydrochloride in methanol as the solvent to obtain the compound,

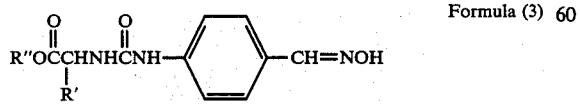

Formula (3)

This compound is then reacted with sodium methylate in methanol, maintaining a pH of about 10 or higher (usual range 9–11) while heating, usually by refluxing, usually for several hours. The solvent methanol is then removed under vacuum, leaving the desired product of formula (1) where R is H.

The products of the present invention where R is hydrocarbyl can be made conveniently by reacting the compound of formula (2) with

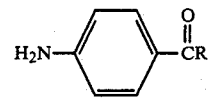

in one of the same solvents (dioxane, THF, etc.) to obtain the compound,

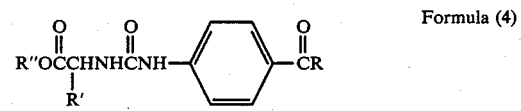

Formula (4)

which is then separated from the solvent. This product is reacted in methanol solvent with hydroxylamine hydrochloride to obtain the compound,

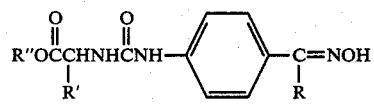

This latter compound is reacted with sodium methylate in methanol, maintaining a pH of about 10 or higher (usual range 9–11) while heating, usually by refluxing for several hours. The solvent methanol is then removed under vacuum, leaving the desired product of Formula (1) where R is hydrocarbyl as before defined.

The starting material isocyanate for either reaction scheme can be made by reacting the compound

Formula (5)

or its hydrochloride with diphosgene in the manner illustrated in the examples herein. In the reaction scheme first described, the starting material acetal for reacting with the isocyanate can conveniently be made by first making the acetal of 4-nitrobenzaldehyde and then hydrogenating such acetal over platinum oxide catalyst to make the corresponding 4-aminobenzaldehyde acetal, all as illustrated in specific examples.

Two examples of the usefulness of the present compound are as follows:

BLOW MOLDED LPDE BOTTLES 1 part substituted hydantoin compound is blended with 1000 parts low density polyethylene in a plasticating screw extruder, pelletized, and blow molded to give a bottle which has substantially reduced UV transparency compared with a bottle made without the hydantoin compound.

POLYETHYLENE SHEET 1 part substituted hydantoin is blended with 1000 parts low-density polyethylene in a plasticating screw extruder and then extrusion blow molded into 4 mil film which exhibits substantially reduced UV transparency compared with film not containing the hydantoin.

The following examples are merely illustrative and are not to be considered as limiting.

EXAMPLE 1

4-nitrobenzaldehyde ethylene glycol acetal is made as follows: A mixture of 75.5 g 4-nitrobenzaldehyde, 100 mL ethylene glycol, and 2.5 g 4-toluenesulfonic acid in 500 mL toluene are heated with stirring to reflux under $N_2$ for 5 hours in a 1000 mL round bottom flask equipped with a Dean-Stark trap and reflux condenser. During this time about 20 mL of a mixture of water and ethylene glycol is collected in the trap. The product mixture is washed with two 100 mL portions of saturated aqueous sodium bicarbonate solution and with 100 mL water. The organic layer is dried over $MgSO_4$, and the solvent is distilled off on rotary evaporator. The resultant yellow solid is recrystallized from ethanol to give a yellow crystalline solid, mp. 87°–88° C., yield=80–85%.

A mixture of 19.5 g of the 4-nitrobenzaldehyde ethylene glycol acetal, 21.2 g trimethyl orthoformate, and 2 g $PtO_2$ in 250 mL anhydrous THF is placed in a 450 mL Parr stirred autoclave. The contents are purged with $N_2$, with the contents kept between 7° and 10° C. by external cooling. 100 psig $H_2$ is pressed in, and the reaction mixture is stirred. The reaction mixture warms to 20° C., and external cooling (ice bath) is maintained. The $H_2$ pressure is maintained at 100 psi by repressurization several times over a 14–18 minute period. The temperature then begins to drop, and little further drop in $H_2$ is noted. The reaction mixture is stirred for a total of 45 minutes, after which time the reaction temperature returns to 7°–10° C. The autoclave is vented and opened, and the pale yellow product solution is filtered, dried over $CaSO_4$, refiltered, and distilled to dryness to rotary evaporator. The product 4-aminobenzaldehyde ethylene glycol acetal, a nearly white solid, is collected in over 90% yield (mp.=71°–73° C.)

DL-alanine methyl ester isocyanate is made as follows: 38.8 mL diphosgene is added dropwise over 1 hour to a mixture of 38.92 g DL-alanine methyl ester hydrochloride and 0.4 g activated charcoal in 400 mL dioxane under $N_2$. The reaction mixture is warmed to 75°–80° C. during this time. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled (bp 70° C., 10 mm Hg) to give pure DL-alanine methyl ester isocyanate in about 60% yield.

N-[4-(hydroxyiminomethyl)phenyl]-N'-(1-methoxycarbonylethyl)urea is prepared as follows: A solution of 0.1 mol of 4-aminobenzaldehyde ethylene glycol acetal in 100 mL of anhydrous THF is added dropwise over 10 minutes to a solution of 0.1 mol and DL-alanine methyl ester isocyanate and 0.35 mol pyridine in 100 mL THF at room temperature under $N_2$. The yellow reaction mixture is stirred at room temperature for 2 hours. After ½ hour a yellow-orange precipitate begins to form. After 2 hours the solvent is removed by rotary evaporator to give an orange, semisolid mass. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. Off-white crystals of product form after 2 hours of stirring. The crystals are isolated by filtration and dried overnight in a vacuum oven at 50°–55° C. The yield of product (mp 143°–145.5° C.) is 60%.

3-[4-(hydroxyiminomethyl)phenyl]-5-methylhydantoin is made as follows: 14.15 g of N-[4-(hydroxyiminomethyl)phenyl]-N'-(1-methoxycarbonylethyl)urea is dissolved in 300 mL of $CH_3OH$. The pH is adjusted to approximately 10.0 using 25% $NaOCH_3$ solution in $CH_3OH$ (appx. 4 mL). The solution is heated to reflux for 2.5 hours, after which time the solvent is removed under vacuum. The residue is washed with cold water and dried in vacuo to yield 9.10 g of the crude hydantoin. The hydantoin is purified by recrystallization from a 17:10:1 w:w:w solution of $CH_3OH$:$H_2O$:hydantoin, mp. 215.0°–216.0° C.

Elemental analysis: calcd. C 56.65, H 4.75, N 18.02; found C 56.63, H 4.72, N 18.04.

$^{13}$C NMR (acetone-$d_6$): δ175, —N$\underline{C}$OCH—; 156, —N$\underline{C}$ON—; 148, —$\underline{C}$H—NOH; 128, 133, 134, phenyl; 53, —$\underline{C}$OCH($CH_3$)N$\overline{H}$—; 18, —$CH_3$.

$^1$H NMR (acetone-$d_6$): δ10.5, s, 1H, —CH=NO$\underline{H}$; 8.2, s, 1H, —C$\underline{H}$=NOH; 7.5, m, 4H, aryl; 4.35, q, 1$\underline{H}$, —C$\underline{H}$CH$_3$; 1.5, d, 3H, —CHC$\underline{H_3}$.

UV-visible ($CH_3OH$): $\lambda_{max}$=262 nm, $\epsilon$=2.32×10$^4$.

EXAMPLE 2

0.35 mol diphosgene is added dropwise over 1 hour to a mixture of 0.28 mol of the dimethyl ester of aspartic acid and 0.4 g activated charcoal in 400 mL dioxane under $N_2$. The reaction mixture is warmed to 75°–80° C. during this time. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give dimethyl aspartate isocyanate.

A solution of 0.1 mol of 4-aminobenzaldehyde ethylene glycol acetal in 100 mL of anhydrous THF is added dropwise over 10 minutes to a solution of 0.1 mol of dimethyl aspartate isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-[1,2-bis(methoxycarbonyl)ethyl]urea forms after several hours of stirring. The product is isolated by filtration and dried overnight in a vacuum oven at 50°–55° C.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed under vacuum. The residue is washed with cold water and dried in vacuo to yield the crude 3-[4-(hydroxyiminomethyl)phenyl]-5-methoxycarbonylmethylhydantoin. The hydantoin is purified by recrystallization from $CH_3OH$:$H_2O$.

EXAMPLE 3

38.8 mL diphosgene is added dropwise over 1 hour to a mixture of 35 g glycine methyl ester hydrochloride and 0.4 g activated charcoal in 400 mL dioxane under $N_2$. The reaction mixture is warmed to 80° C. during this time. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give pure glycine methyl ester isocyanate in about 70% yield (b.p. 60° C., 13 mm Hg).

A solution of 0.1 mol of 4-aminobenzaldehyde ethylene glycol acetal in 100 mL of anhydrous THF is added dropwise over 10 minutes to a solution of 0.1 mol of glycine methyl ester isocyanate and 0.35 mol pyridine in 100 mL THF at room temperature under $N_2$. The yellow reaction mixture was stirred at room temperature for 2 hours. After ½ hour a yellow-orange precipitate begins to form. After 2 hours the solvent is removed by rotary evaporator to give an orange semisolid mass. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. Pale yellow crystals of N-[4-(hydroxyiminomethyl)phenyl]-N'-(methoxycarbonylmethyl)urea forms after ½ hour of stirring. The product is isolated by filtration and dried overnight in a vacuum oven at 50°–55° C.

The product is purified by recrystallization from a 10:6:1 solution of $CH_3OH:H_2O$: compound. The product is washed with cold water and dried in a vacuum oven at 50° C. to give off-white crystals, mp. 167.5°–168.5° C.

Elemental analysis: calcd. C 52.59, H 5.22, N 16.72; found C 52.38, H 5.16, N 16.65.

$^1H$ NMR (acetone-$d_6$): δ10.15 s, 1H, —NOH; 8.4 s, 1H, —NH—; 8.1 s/d, 1H, —CH=N; 7.55 bs, 4H, phenyl; 6.21 s/d, 1H, —NH—; 4.02 s/d, 2H, —CH$_2$—; 3.74 s, 3H, CH$_3$O—.

$^{13}C$ NMR (acetone-$d_6$): δ172, —COO—; 156, —N-CON—; 149, —CH=N—; 119, 128, 142, phenyl; 52, CH$_3$O—; 42, —CH$_2$—.

UV-vis ($CH_3OH$): $\lambda_{max}$=279 nm, $\epsilon$=2.90×10$^4$.

0.02 mol of this urea is dissolved in 300 mL of $CH_3OH$. The pH is adjusted to approximately 10.0 using 25% NaOCH$_3$ solution in $CH_3OH$. The solution is heated to reflux for 2.5 hours, after which time the solvent is removed under vacuum. The residue is washed with cold water and dried in vacuo to yield the crude 3-[4-(hydroxyiminomethyl)phenyl]hydantoin. The hydantoin is purified by recrystallization from $CH_3OH:H_2O$.

EXAMPLE 4

0.35 mol diphosgene is added dropwise over 1 hour to a mixture of 0.28 mol of the dimethyl ester of glutamic acid and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give dimethyl glutamate isocyanate.

A solution of 0.1 mol of 4-aminobenzaldehyde ethylene glycol acetal in 100 mL of anhydrous THF is added dropwise over 10 minutes to a solution of 0.1 mol of dimethyl glutamate isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-[1,3-bis(-methoxycarbonyl)propyl]urea forms after several hours of stirring. The product is isolated by filtration and dried overnight in a vacuum oven at 50°–55° C.

0.02 mol of this urea is dissolved in 300 mL of $CH_3OH$. The pH is adjusted to approximately 10.0 using 25% NaOCH$_3$ solution in $CH_3OH$. The solution is heated to reflux for 2.5 hours, after which time the solvent is removed under vacuum. The residue is washed with cold water and dried in vacuo to yield the crude 3-[4-(hydroxyiminomethyl)phenyl]-5-(2-methoxycarbonylethyl)hydantoin. The hydantoin is purified by recrystallization from $CH_3OH:H_2O$.

EXAMPLE 5

0.35 mol diphosgene is added dropwise over 1 hour to a mixture of 0.28 mol of the methyl ester of valine and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give valine methyl ester isocyanate.

A solution of 0.1 mol of 4-aminobenzaldehyde ethylene glycol acetal in 100 mL of anhydrous THF is added dropwise over 10 minutes to a solution of 0.1 mol of valine methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroximinomethyl)phenyl]-N'-[1-(1-methoxycarbonyl-2-methyl)propyl]urea forms after several hours of stirring. The product is isolated by filtration and dried overnight in a vacuum oven at 50°–55° C.

0.02 mol of this urea is dissolved in 300 mL of $CH_3OH$. The pH is adjusted to approximately 10.0 using 25% NaOCH$_3$ solution in $CH_3OH$. The solution is heated to reflux for 2.5 hours, after which time the solvent is removed under vacuum. The residue is washed with cold water and dried in vacuo to yield the crude 3-[4-(hydroxyiminomethyl)phenyl]-5-isopropylhydantoin.

The hydantoin is purified by recrystallization from $CH_3OH{:}H_2O$.

EXAMPLE 6

0.35 mol diphosgene is added dropwise over 1 hour to a mixture of 0.28 mol of the methyl ester of leucine and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give leucine methyl ester isocyanate.

A solution of 0.1 mol of 4-aminobenzaldehyde ethylene glycol acetal in 100 mL of anhydrous THF is added dropwise over 10 minutes to a solution of 0.1 mol of leucine methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-(1-methoxycarbonyl-3-methylbutyl)urea forms after several hours of stirring. The product is isolated by filtration and dried overnight in a vacuum oven at 50°–55° C.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed under vacuum. The residue is washed with cold water and dried in vacuo to yield the crude 3-[4-(hydroxyiminomethyl)phenyl]-5-isobutylhydantoin.

The hydantoin is purified by recrystallization from $CH_3OH{:}H_2O$.

EXAMPLE 7

0.35 mol diphosgene is added dropwise over 1 hour to a mixture of 0.28 mol of the methyl ester of isoleucine and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give isoleucine methyl ester isocyanate.

A solution of 0.1 mol of 4-aminobenzaldehyde ethylene glycol acetal in 100 mL of anhydrous THF is added dropwise over 10 minutes to a solution of 0.1 mol of isoleucine methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-(1-methoxycarbonyl-2-methylbutyl)urea forms after several hours of stirring. The product is isolated by filtration and dried overnight in a vacuum oven at 50°–55° C.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed under vacuum. The residue is washed with cold water and dried in vacuo to yield the crude 3-[4-(hydroxyiminomethyl)phenyl]-5-sec-butylhydantoin.

The hydantoin is purified by recrystallization from $CH_3OH{:}H_2O$.

EXAMPLE 8

0.35 mol diphosgene is added dropwise over 1 hour to a mixture of 0.28 mol of the methyl ester of methionine and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give methionine methyl ester isocyanate.

A solution of 0.1 mol of 4-aminobenzaldehyde ethylene glycol acetal in 100 mL of anhydrous THF is added dropwise over 10 minutes to a solution of 0.1 mol of methionine methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-(1-methoxycarbonyl-3-methylthiopropyl)urea forms after several hours of stirring. The product is isolated by filtration and dried overnight in a vacuum oven at 50°–55° C.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed under vacuum. The residue is washed with cold water and dried in vacuo to yield the crude 3-[4-(hydroxyiminomethyl)phenyl]-5-(2-methylthioethyl)hydantoin.

The hydantoin is purified by recrystallization from $CH_3OH{:}H_2O$.

EXAMPLE 9

0.35 mol diphosgene is added dropwise over 1 hour to a mixture of 0.28 mol of the methyl ester of phenylalanine and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give phenylalanine methyl ester isocyanate.

A solution of 0.1 mol of 4-aminobenzaldehyde ethylene glycol acetal in 100 mL of anhydrous THF is added dropwise over 10 minutes to a solution of 0.1 mol of phenylalanine methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-(1-methoxycarbonyl-2-phenylethyl)urea forms after several hours of stirring. The product is isolated by filtration and dried overnight in a vacuum oven at 50°–55° C.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed under vacuum. The residue is washed with cold water and dried in vacuo to yield the crude 3-[4-(hydroxyiminomethyl)phenyl]-5-benzylhydantoin.

The hydantoin is purified by recrystallization from $CH_3OH:H_2O$.

EXAMPLE 10

0.35 mol diphosgene is added dropwise over 1 hour to a mixture of 0.28 mol of the methyl ester of 2-amino-3-(1-acetyl-3-indole)propanoic acid and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give 2-isocyanato-3-(1-acetyl-3-indole)propanoic acid methyl ester.

A solution of 0.1 mol of 4-aminobenzaldehyde ethylene glycol acetal in 100 mL of anhydrous THF is added dropwise over 10 minutes to a solution of 0.1 mol of 2-isocyanato-3-(1-acetyl-3-indole)propanoic acid methyl ester and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-[1-methoxycarbonyl-2-(1-acetyl-3-indolyl)ethyl]urea forms after several hours of stirring. The product is isolated by filtration and dried overnight in a vacuum oven at 50°–55° C.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed under vacuum. The residue is washed with cold water and dried in vacuo to yield the crude 3-[4-(hydroxyiminomethyl)phenyl]-5-(1-acetyl-3-indolyl)methylhydantoin.

The hydantoin is purified by recrystallization from $CH_3OH:H_2O$.

EXAMPLE 11

0.35 mol diphosgene is added dropwise over 1 hour to a mixture of 0.28 mol of the methyl ester of 0-acetylserine and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give 0-acetylserine methyl ester isocyanate.

A solution of 0.1 mol of 4-aminobenzaldehyde ethylene glycol acetal in 100 mL of anhydrous THF is added dropwise over 10 minutes to a solution of 0.1 mol of 0-acetylserine methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-(1-methoxycarbonyl-2-acetyloxyethyl)urea forms after several hours of stirring. The product is isolated by filtration and dried overnight in a vacuum oven at 50°–55° C.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed under vacuum. The residue is washed with cold water and dried in vacuo to yield the crude 3-[4-(hydroxyiminomethyl)phenyl]-5-acetyloxymethylhydantoin.

The hydantoin is purified by recrystallization from $CH_3OH:H_2O$.

EXAMPLE 12

0.35 mol diphosgene is added dropwise over 1 hour to a mixture of 0.28 mol of the methyl ester of 0-acetylthreonine and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give 0-acetylthreonine methyl ester isocyanate.

A solution of 0.1 mol of 4-aminobenzaldehyde ethylene glycol acetal in 100 mL of anhydrous THF is added dropwise over 10 minutes to a solution of 0.1 mol of 0-acetylthreonine methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. N-[4-(hydroxyiminomethyl)phenyl]-N'-(1-methoxycarbonyl-2-acetyloxypropyl)urea forms after several hours of stirring. The product is isolated by filtration and dried overnight in a vacuum oven at 50°-55° C.

0.02 mol of this urea is dissolved in 300 mL of CH₃OH. The pH is adjusted to approximately 10.0 using 25% NaOCH₃ solution in CH₃OH. The solution is heated to reflux for 2.5 hours, after which time the solvent is removed under vacuum. The residue is washed with cold water and dried in vacuo to yield the crude 3-[4-(hydroxyiminomethyl)phenyl]-5-(1-acetyloxyethyl)hydantoin.

The hydantoin is purified by recrystallization from CH₃OH:H₂O.

EXAMPLE 13

0.35 mol diphosgene is added dropwise over 1 hour to a mixture of 0.28 mol of the methyl ester of S-acetylcysteine and 0.4 g activated charcoal in 400 mL dioxane under N₂. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5-6.0 by addition of pyridine. The product mixture is again filtered, and the filtrate is fractionally distilled to give S-acetylcysteine methyl ester isocyanate.

A solution of 0.1 mol of 4-aminobenzaldehyde ethylene glycol acetal in 100 mL of anhydrous THF is added dropwise over 10 minutes to a solution of 0.1 mol of S-acetylcysteine methyl ester isocyanate and 0.35 mol pyridine in 100 mL THF at room temperature under N₂. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. N-[4-(hydroxyiminomethyl)phenyl]-N'-[1-methoxycarbonyl-2-(acetylthio)ethyl]urea forms after several hours of stirring. The product is isolated by filtration and dried overnight in a vacuum oven at 50°55° C.

0.02 mol of this urea is dissolved in 300 mL of CH₃OH. The pH is adjusted to approximately 10.0 using 25% NaOCH₃ solution in CH₃OH. The solution is heated to reflux for 2.5 hours, after which time the solvent is removed under vacuum. The residue is washed with cold water and dried in vacuo to yield the crude 3-[4-(hydroxyiminomethyl)phenyl]-5-acetylthiomethylhydantoin.

The hydantoin is purified by recrystallization from CH₃OH:H₂O.

EXAMPLE 14

0.35 mol diphosgene is added dropwise over 1 hour to a mixture of 0.28 mol of the methyl ester of O-acetyltyrosine and 0.4 g activated charcoal in 400 mL dioxane under N₂. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5-6.0 by addition of pyridine. The product mixture is again filtered, and the filtrate is fractionally distilled to give O-acetyltyrosine methyl ester isocyanate.

A solution of 0.1 mol of 4-aminobenzaldehyde ethylene glycol acetal in 100 mL of anhydrous THF is added dropwise over 10 minutes to a solution of 0.1 mol of O-acetyltyrosine methyl ester isocyanate and 0.35 mol pyridine in 100 mL THF at room temperature under N₂. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. N-[4-(hydroxyiminomethyl)phenyl]-N'-[1-methoxycarbonyl-2-(4-acetyloxyphenyl)ethyl]urea forms after several hours of stirring. The product is isolated by filtration and dried overnight in a vacuum oven at 50°-55° C.

0.02 mol of this urea is dissolved in 300 mL of CH₃OH. The pH is adjusted to approximately 10.0 using 25% NaOCH₃ solution in CH₃OH. The solution is heated to reflux for 2.5 hours, after which time the solvent is removed under vacuum. The residue is washed with cold water and dried in vacuo to yield the crude 3-[4-(hydroxyiminomethyl)phenyl]-5-(4-acetyloxyphenyl)methylhydantoin.

The hydantoin is purified by recrystallization from CH₃OH:H₂O.

EXAMPLE 15

0.35 mol diphosgene is added dropwise over 1 hour to a mixture of 0.28 mol of the methyl ester of asparagine and 0.4 g activated charcoal in 400 mL dioxane under N₂. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5-6.0 by addition of pyridine. The product mixture is again filtered, and the filtrate is fractionally distilled to give asparagine methyl ester isocyanate.

A solution of 0.1 mol of 4-aminobenzaldehyde ethylene glycol acetal in 100 mL of anhydrous THF is added dropwise over 10 minutes to a solution of 0.1 mol of asparagine methyl ester isocyanate and 0.35 mol pyridine in 100 mL THF at room temperature under N₂. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. N-[4-(hydroxyiminomethyl)phenyl]-N'-(1-methoxycarbonyl-2-carbamoylethyl)urea forms after several hours of stirring. The product is isolated by filtration and dried overnight in a vacuum oven at 50°-55° C.

0.02 mol of this urea is dissolved in 300 mL of CH₃OH. The pH is adjusted to approximately 10.0 using 25% NaOCH₃ solution in CH₃OH. The solution is heated to reflux for 2.5 hours, after which time the solvent is removed under vacuum. The residue is washed with cold water and dried in vacuo to yield the crude 3-[4-(hydroxyiminomethyl)phenyl]-5-carbamoylmethylhydantoin.

The hydantoin is purified by recrystallization from $CH_3OH:H_2O$.

EXAMPLE 16

0.35 mol diphosgene is added dropwise over 1 hour to a mixture of 0.28 mol of the methyl ester of glutamine and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give glutamine methyl ester isocyanate.

A solution of 0.1 mol of 4-aminobenzaldehyde ethylene glycol acetal in 100 mL of anhydrous THF is added dropwise over 10 minutes to a solution of 0.1 mol of glutamine methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-(1-methoxycarbonyl-3-carbamoylpropyl)urea forms after several hours of stirring. The product is isolated by filtration and dried overnight in a vacuum oven at 50°–55° C.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed under vacuum. The residue is washed with cold water and dried in vacuo to yield the crude 3-[4-(hydroxyiminomethyl)phenyl]-5-(2-carbamoylethyl)hydantoin.

The hydantoin is purified by recrystallization from $CH_3OH:H_2O$.

EXAMPLE 17

0.35 mol diphosgene is added dropwise over 1 hour to a mixture of 0.28 mol of the methyl ester of ε-N-acetyllysine and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give ε-N-acetyllysine methyl ester isocyanate.

A solution of 0.1 mol of 4-aminobenzaldehyde ethylene glycol acetal in 100 mL of anhydrous THF is added dropwise over 10 minutes to a solution of 0.1 mol of ε-N-acetyllysine methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-(1-methoxycarbonyl-5-acetamidopentyl)urea forms after several hours of stirring. The product is isolated by filtration and dried overnight in a vacuum oven at 50°–55° C.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed under vacuum. The residue is washed with cold water and dried in vacuo to yield the crude 3-[4-(hydroxyiminomethyl)phenyl]-5-(4-acetamidobutyl)hydantoin.

The hydantoin is purified by recrystallization from $CH_3OH:H_2O$.

EXAMPLE 18

0.35 mol diphosgene is added dropwise over 1 hour to a mixture of 0.28 mol of the methyl ester of 2-amino-3-(3-acetyl-5-imidazole)propanoic acid and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give 2-isocyanato-3-(3-acetyl-5-imidazole)propanoic acid methyl ester.

A solution of 0.1 mol of 4-aminobenzaldehyde ethylene glycol acetal in 100 mL of anhydrous THF is added dropwise over 10 minutes to a solution of 0.1 mol of 2-isocyanato-3-(3-acetyl-5-imidazole)propanoic acid methyl ester and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-[1-methoxycarbonyl-2-(3-acetyl-5-imidazolyl)ethyl]urea forms after several hours of stirring. The product is isolated by filtration and dried overnight in a vacuum oven at 50°–55° C.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed under vacuum. The residue is washed with cold water and dried in vacuo to yield the crude 3-[4-(hydroxyiminomethyl)phenyl]-5-[(3-acetyl-5-imidazolyl)methyl]hydantoin.

The hydantoin is purified by recrystallization from $CH_3OH:H_2O$.

EXAMPLE 19

9.7 mL diphosgene is added dropwise over 50 minutes to a mixture of 12.85 g dimethyl aminomalonate hydrochloride and 0.1 g activated charcoal in 25 mL dioxane under $N_2$. The reaction mixture is warmed to 75°–80° C. during this time. The reaction mixture is then heated and stirred at reflux for 2½ hours. The reaction mixture is then cooled, filtered, and concentrated to dryness by rotary evaporator, keeping exposure to moisture to a minimum. The crude product is purified by fractional distillation (bp 80°–85° C., <1 mm Hg) to give pure dimethyl isocyanatomalonate in >80% yield.

N-[4-(hydroxyiminomethyl)phenyl]-N'-bis(methoxycarbonyl)methylurea is made as follows: A solution of 0.1 mol of 4-aminobenzaldehyde ethylene glycol acetal in 100 mL of anhydrous THF is added dropwise over 10 minutes to a solution of 0.1 mol of the dimethyl aminomalonate isocyanate and 0.35 mol pyridine in 100 mL THF at room temperature under $N_2$. The yellow reaction mixture is stirred at room temperature for 2 hours. After ½ hour a precipitate begins to form. After 2 hours the solvent is removed by rotary evaporator to give a yellow, semisolid mass. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. Off-white crystals of product form, which are isolated by filtration and dried overnight in a vacuum oven at 50°–55° C. The yield of crude product (mp 164°–166° C.): 75–80%.

The product is purified by multiple extraction with ethanol until the washings are no longer yellow. White crystals, m.p. 161.5°–162.5° C.

Elemental analysis: calcd. C 50.49, N 4.89, N 13.59; found C 50.88, H 4.90, N 13.52.

$^1$H NMR (acetone-$d_6$ - DMSO-$d_6$): $\delta$10.95 s, 1H, —NOH; 9.1s, 1H, —NH—; 8.1s, 1H, —CH=N—; 7.55 bs, 4H, phenyl; 7.15 d, 1H, —NH—; 5.15 s/d, 1H, —CH—; 3.80 s, 3H, $CH_3O$—.

$^{13}$C NMR (acetone-$d_6$-DMSO-$d_6$): $\delta$168, —COO—; 155, —NCON—; 148, —CH=N—; 118, 128, 142, phenyl; 58, —$CH_2$—; 53, $CH_3O$—. UV-vis ($CH_3OH$): $\lambda_{max}$-276 nm, $\epsilon$=3.06×10$^4$.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed under vacuum. The residue is washed with cold water and dried in vacuo to yield the crude 3-[4-hydroxyiminomethyl)phenyl]-5-methoxycarbonylhydantoin.

The hydantoin is purified by recrystallization from $CH_3OH:H_2O$.

EXAMPLE 20

3-[4-(1-hydroxyiminoethyl)phenyl]hydantoin is made as follows: a solution of 2.7 g p-aminoacetophenone in 40 mL THF is added dropwise to a solution of 2.3 g glycine methyl ester isocyanate and 5 mL pyridine in 40 mL THF, and the reaction mixture is stirred for 3 hours. The solvent is then removed by rotary evaporator to leave an off-white solid. The solid is dispersed in 50 mL $CH_3OH$, and 1.53 g hydroxylamine hydrochloride and 6.4 g trimethyl orthoformate are added. The reaction mixture is heated to reflux for 1 hour. The solvent is removed by rotary evaporator to leave an orange oil. Addition of water to the oil results in formation of off-white crystals. The crystals are treated again with 1,0 g hydroxylamine hydrochloride and 3.0 g trimethyl orthoformate in 50 mL $CH_3OH$ at reflux for 1 hour. The product mixture is then treated with $NaOCH_3$ in $CH_3OH$ to adjust the pH of the solution to 7. The product mixture is then concentrated by rotary evaporator, water is added, and the solid which forms (mp. 179°–181° C. dec.) is shown by $^1$H NMR spectroscopy (acetone-$d_6$/DMSO-$d_6$) to contain the hydantoin product.

$^1$H NMR resonances assignable to the hydantoin include: $\delta$4.1 s, 2H, —$COCH_2$—NH—; 2.25 s, 3H, HON=C($CH_3$)—.

The foregoing run is repeated except that the step of adjusting the pH is omitted. The solid product has a mp of 179°–181° C. dec. and is shown by NMR spectroscopy to be pure N-[4-(1-hydroxyiminoethyl)phenyl]-N'-methoxycarbonylmethylurea.

EXAMPLE 21

A solution of 0.02 mol 4-aminoacetophenone in 40 mL THF is added dropwise to a solution of 0.02 mol of dimethyl aspartate isocyanate and 5 mL pyridine in 40 mL THF, and the reaction mixture is stirred for 3 hours. The solvent is then removed by rotary evaporator. The residue is dispersed in 50 mL $CH_3OH$, and 0.022 mol hydroxylamine hydrochloride and 0.06 mol trimethyl orthoformate are added. The reaction mixture is heated to reflux for 1 hour. The solvent is removed by rotary evaporator. Addition of water to the residue results in formation of crystals of N-[4-(1-hydroxyiminoethyl)phenyl]-N'-[1,2-bis(methoxycarbonyl)ethyl]urea, which is treated with $NaOCH_3$ in $CH_3OH$ to adjust the pH to 10. The solution is heated to reflux for 2.5 hours, and then the solvent is removed under vacuum. The solid remaining is washed with cold water to yield 3-[4-(1-hydroxyiminoethyl)phenyl]-5-methoxycarbonylmethylhydantoin.

The hydantoin is purified by recrystallization from $CH_3OH:H_2O$.

EXAMPLE 22

A solution of 0.02 mol 4-aminoacetophenone to 40 mL THF is added dropwise to a solution of 0.02 mol of dimethyl glutamate isocyanate and 5 mL pyridine in 40 mL THF, and the reaction mixture is stirred for 3 hours. The solvent is then removed by rotary evaporator. The residue is dispersed in 50 mL $CH_3OH$, and 0.022 mol hydroxylamine and 0.06 mol trimethyl orthoformate are added. The reaction mixture is heated to reflux for 1 hour. The solvent is removed by rotary evaporator. Addition of water to the residue results in formation of crystals of N-[4-(1-hydroxyiminoethyl)phenyl]-N'-[1,3-bis(methoxycarbonyl)propyl]urea, which is then treated with $NaOCH_3$ in $CH_3OH$ to adjust the pH to 10. The solution is heated to reflux for 2.5 hours, and the solvent is removed under vacuum. The residue is washed with cold water to yield 3-[4-(1-hydroxyiminoethyl)phenyl]-5-(2-methoxycarbonylethyl)hydantoin.

The hydantoin is purified by recrystallization for $CH_3OH:H_2O$.

EXAMPLE 23

A solution of 0.02 mol 4-aminoacetophenone in 40 mL THF is added dropwise to a solution of 0.02 mol of valine methyl ester isocyanate and 5 mL pyridine in 40 mL THF, and the reaction mixture is stirred for 3 hours. The solvent is then removed by rotary evaporator. The residue is dispersed in 50 mL $CH_3OH$, and 0.022 mol hydroxylamine hydrochloride and 0.06 mol trimethyl orthoformate are added. The reaction mixture is heated to reflux for 1 hour. The solvent is removed by rotary evaporator. Addition of water to the residue results in formation of crystals of N-[4-(1-hydroxyiminoethyl)- phenyl]-N'-(1-methoxycarbonyl-2-methylpropyl)urea, which is then treated with NaOCH$_3$ to adjust the pH to 10. The solution is heated to reflux for 2.5 hours, and the solvent is removed under vacuum. The residue is washed with cold water to yield 3-[4-(1-hydroxyiminoethyl)phenyl]-5-isopropylhydantoin. The hydantoin is purified by recrystallization from CH$_3$OH:H$_2$O.

EXAMPLE 24

A solution of 0.02 mol 4-aminoacetophenone in 40 mL THF is added dropwise to a solution of 0.02 mol of leucine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 1 hour. The solvent is removed by rotary evaporator. Addition of water to the residue results in precipitation of N-[4-(1-hydroxyiminoethyl)phenyl]-N'-(1-methoxycarbonyl-3-methylbutyl)urea, which is then treated with NaOCH$_3$ to adjust the pH to 10. The solution is heated to reflux for 2.5 hours, and the solvent is removed under vacuum. The residue is washed with cold water to yield the crude 3-[4-(1-hydroxyiminoethyl)phenyl]-5-isobutylhydantoin. The hydantoin is purified by recrystallization from CH$_3$OH:H$_2$O.

EXAMPLE 25

A solution of 0.02 mol 4-aminoacetophenone in 40 mL THF is added dropwise to a solution of 0.02 mol of isoleucine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 1 hour. The solvent is removed by rotary evaporator. Addition of water to the residue results in precipitation of N-[4-(1-hydroxyiminoethyl)phenyl]-N'-(1-methoxycarbonyl-2-methylbutyl)urea, which is then treated with NaOCH$_3$ to adjust the pH to 10. The solution is heated to reflux for 2.5 hours, and the solvent is removed under vacuum. The residue is washed with cold water to yield the crude 3-[4-(1-hydroxyiminoethyl)phenyl]-5-sec-butylhydantoin. The hydantoin is purified by recrystallization from CH$_3$OH:H$_2$O.

EXAMPLE 26

A solution of 0.02 mol 4-aminoacetophenone in 40 mL THF is added dropwise to a solution of 0.02 mol of the methionine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 1 hour. The solvent is removed by rotary evaporator. Addition of water to the residue results in precipitation of N-[4-(1-hydroxyiminoethyl)phenyl]-N'-(1-methoxycarbonyl-3-methylthiopropyl)urea, which is then treated with NaOCH$_3$ to adjust the pH to 10. The solution is heated to reflux for 2.5 hours, and the solvent is removed under vacuum. The residue is washed with cold water to yield the crude 3-[4-(1-hydroxyiminoethyl)phenyl]-5-(2-methylthioethyl)hydantoin. The hydantoin is purified by recrystallization from CH$_3$OH:H$_2$O.

EXAMPLE 27

A solution of 0.02 mol 4-aminoacetophenone in 40 mL THF is added dropwise to a solution of 0.02 mol of phenylalanine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 1 hour. The solvent is removed by rotary evaporator. Addition of water to the residue results in precipitation of N-[4-(1-hydroxyiminoethyl)phenyl]-N'-(1-methoxycarbonyl-2-phenylethyl)urea, which is then treated with NaOCH$_3$ to adjust the pH to 10. The solution is heated to reflux for 2.5 hours, and the solvent is removed under vacuum. The residue is washed with cold water to yield the crude 3-[4-(1-hydroxyiminoethyl)phenyl]-5-benzylhydantoin. The hydantoin is purified by recrystallization from CH$_3$OH:H$_2$O.

EXAMPLE 28

A solution of 0.02 mol 4-aminoacetophenone in 40 mL THF is added dropwise to a solution of 0.02 mol of 2-isocyanato-3-(1-acetyl-3-indole)propanoic acid methyl ester and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 1 hour. The solvent is removed by rotary evaporator. Addition of water to the residue results in precipitation of N-[4-(1-hydroxyiminoethyl)phenyl]-N'-[1-methoxycarbonyl-2-(1-acetyl-3-indolyl)ethyl]urea, which is then treated with NaOCH$_3$ to adjust the pH to 10. The solution is heated to reflux for 2.5 hours, and the solvent is removed under vacuum. The residue is washed with cold water to yield the crude 3-[4-(1-hydroxyiminoethyl)phenyl]-5-[(1-acetyl-3-indolyl)methyl]hydantoin. The hydantoin is purified by recrystallization from CH$_3$OH:H$_2$O.

EXAMPLE 29

A solution of 0.02 mol 4-aminoacetophenone in 40 mL THF is added dropwise to a solution of 0.02 mol of 0-acetylserine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 1 hour. The solvent is removed by rotary evaporator. Addition of water to the residue results in precipitation of N-[4-(1-hydroxyiminoethyl)phenyl]-N'-(1-methoxycarbonyl-2-acetyloxyethyl)urea, which is then treated with NaOCH$_3$ to adjust the pH to 10. The solution is heated to reflux for 2.5 hours, and the solvent is removed under vacuum. The residue is washed with cold water to yield the crude 3-[4-(1-hydroxyiminoethyl)phenyl]-5-acetyloxymethylhydantoin. The hydantoin is purified by recrystallization from CH$_3$OH:H$_2$O.

Example 30

A solution of 0.02 mol 4-aminoacetophenone in 40 mL THF is added dropwise to a solution of 0.02 mol of 0-acetylthreonine methyl ester isocyanate and 5 mL pyridine in 40 mL THF, and the reaction mixture is stirred for 3 hours. The solvent is then removed by rotary evaporator. The residue is dispersed in 50 mL $CH_3OH$, and 0.022 mol hydroxylamine hydrochloride and 0.06 mol trimethyl orthoformate are added. The reaction mixture is heated to reflux for 1 hour. The solvent is removed by rotary evaporator. Addition of water to the residue results in precipitation of N-[4-(1-hydroxyiminoethyl)phenyl]-N'-(1-methoxycarbonyl-2-acetyloxypropyl)urea, which is then treated with $NaOCH_3$ to adjust the pH to 10. The solution is heated to reflux for 2.5 hours, and the solvent is removed under vacuum. The residue is washed with cold water to yield the crude 3-[4-(1-hydroxyiminoethyl)phenyl]-5-(1-acetyloxyethyl)hydantoin. The hydantoin is purified by recrystallization from $CH_3OH:H_2O$.

EXAMPLE 31

A solution of 0.02 mol 4-aminoacetophenone in 40 mL THF is added dropwise to a solution of 0.02 mol of S-acetylcysteine methyl ester isocyanate and 5 mL pyridine in 40 mL THF, and the reaction mixture is stirred for 3 hours. The solvent is then removed by rotary evaporator. The residue is dispersed in 50 mL $CH_3OH$, and 0.022 mol hydroxylamine hydrochloride and 0.06 mol trimethyl orthoformate are added. The reaction mixture is heated to reflux for 1 hour. The solvent is removed by rotary evaporator. Addition of water to the residue results in precipitation of N-[4-(1-hydroxyiminoethyl)phenyl]-N'-[1-methoxycarbonyl-2-(acetylthio)ethyl]urea, which is then treated with $NaOCH_3$ to adjust the pH to 10. The solution is heated to reflux for 2.5 hours, and the solvent is removed under vacuum. The residue is washed with cold water to yield the crude 3-[4-(1-hydroxyiminoethyl)phenyl]-5-(acetylthiomethyl)hydantoin. The hydantoin is purified by recrystallization from $CH_3OH:H_2O$.

EXAMPLE 32

A solution of 0.02 mol 4-aminoacetophenone in 40 mL THF is added dropwise to a solution of 0.02 mol of 0-acetyltyrosine methyl ester isocyanate and 5 mL pyridine in 40 mL THF, and the reaction mixture is stirred for 3 hours. The solvent is then removed by rotary evaporator. The residue is dipersed in 50 ml $CH_3OH$, and ) 0.022 mol hydroxylamine hydrochloride and 0.06 mol trimethyl orthoformate are added. The reaction mixture is heated to reflux for 1 hour. The solvent is removed by rotary evaporator. Addition of water to the residue results in precipitation of N-[4-(1-hydroxyiminoethyl)phenyl]-N'-[1-methoxycarbonyl-2-(4-acetyloxyphenyl)ethyl]urea, which is then treated with $NaOCH_3$ to adjust the pH to 10. The solution is heated to reflux for 2.5 hours, and the solvent is removed under vacuum. The residue is washed with cold water to yield the crude 3-[4-(1-hydroxyiminoethyl)phenyl]-5-(4-acetyloxyphenyl)methylhydantoin. The hydantoin is purified by recrystallization from $CH_3OH:H_2O$.

EXAMPLE 33

A solution of 0.02 mol 4-aminoacetophenone in 40 mL THF is added dropwise to a solution of 0.02 mol of asparagine methyl ester isocyanate and 5 mL pyridine in 40 mL THF, and the reaction mixture is stirred for 3 hours. The solvent is then removed by rotary evaporator. The residue is dispersed in 50 mL $CH_3OH$, and 0.022 mol hydroxylamine hydrochloride and 0.06 mol trimethyl orthoformate are added. The reaction mixture is heated to reflux for 1 hour. The solvent is removed by rotary evaporator. Addition of water to the residue results in precipitation of N-[4-(1-hydroxyiminoethyl)phenyl]-N'-(1-methoxycarbonyl-2-carbamoylethyl)urea, which is then treated with $NaOCH_3$ to adjust the pH to 10. The solution is heated to reflux for 2.5 hours, and the solvent is removed under vacuum. The residue is washed with cold water to yield the crude 3-[4-(1-hydroxyiminoethyl)phenyl]-5-carbamoylmethylhydantoin. The hydantoin is purified by recrystallization from $CH_3OH:H_2O$.

EXAMPLE 34

A solution of 0.02 mol 4-aminoacetophenone in 40 mL THF is added dropwise to a solution of 0.02 mol of glutamine methyl ester isocyanate and 5 mL pyridine in 40 mL THF, and the reaction mixture is stirred for 3 hours. The solvent is then removed by rotary evaporator.The residue is dispersed in 50 mL $CH_3OH$, and 0.022 mol hydroxylamine hydrochloride and 0.06 mol trimethyl orthoformate are added. The reaction mixture is heated to reflux for 1 hour. The solvent is removed by rotary evaporator. Addition of water to the residue results in precipitation of N-[4-(1-hydroxyiminoethyl)phenyl]-N'-(1-methoxycarbonyl-3-carbamoylpropyl)urea, which is then treated with $NaOCH_3$ to adjust the pH to 10. The solution is heated to reflux for 2.5 hours, and the solvent is removed under vacuum. The residue is washed with cold water to yield the crude 3-[4-(1-hydroxyiminoethyl)phenyl]-5-(2-carbamoylethyl)hydantoin. The hydantoin is purified by recrystallization from $CH_3OH:H_2O$.

EXAMPLE 35

A solution of 0.02 mol 4-aminoacetophenone in 40 mL THF is added dropwise to a solution of 0.02 mol of ε-N-acetyllysine methyl ester isocyanate and 5 mL pyridine in 40 mL THF, and the reaction mixture is stirred for 3 hours. The solvent is then removed by rotary evaporator. The residue is dispersed in 50 mL $CH_3OH$, and 0.022 mol hydroxylamine hydrochloride and 0.06 mol trimethyl orthoformate are added. The reaction mixture is heated to reflux for 1 hour. The solvent is removed by rotary evaporator. Addition of water to the residue results in precipitation N-[4-(1-hydroxyiminoethyl)phenyl]-N'-(1-methoxycarbonyl-5-acetamidopentyl)urea, which is then treated with $NaOCH_3$ to adjust the pH to 10. The solution is heated to reflux for 2.5 hours, and the solvent is removed under vacuum. The residue is washed with cold water to yield the crude 3-[4-(1-hydroxyiminoethyl)phenyl]-5-(4-acetamidobutyl)hydantoin. The hydantoin is purified by recrystallization from $CH_3OH:H_2O$.

EXAMPLE 36

A solution of 0.02 mol 4-aminoacetophenone in 40 mL THF is added dropwise to a solution of 0.02 mol of 2-isocyanto-3-(3-acetyl-5-imidazole)propanoic acid methyl ester and 5 mL pyridine in 40 mL THF, and the reaction mixture is stirred for 3 hours. The solvent is then removed by rotary evaporator. The residue is dispersed in 50 mL $CH_3OH$, and 0.022 mol hydroxylamine hydrochloride and 0.06 mol trimethyl orthoformate are added. The reaction mixture is heated to reflux for 1 hour. The solvent is removed by rotary evaporator. Addition of water to the residue results in precipitation of N-[4-(1-hydroxyiminoethyl)phenyl]-N'-[1-methoxycarbonyl-2-(3-acetyl-5-imidazolyl)ethyl]urea, which is then treated with NaOCH₃ to adjust the pH to 10. The solution is heated to reflux for 2.5 hours, and the solvent is removed under vacuum. The residue is washed with cold water to yield the crude 3-[4-(1-hydroxyiminoethyl)phenyl]-5-[(3-acetyl-5-imidazolyl)methyl]hydantoin. The hydantoin is purified by recrystallization from CH₃OH:H₂O.

EXAMPLE 37

A solution of 0.02 mol 4-aminoacetophenone in 40 mL THF is added dropwise to a solution of 0.02 mol of alanine methyl ester isocyanate and 5 mL pyridine in 40 mL THF, and the reaction mixture is stirred for 3 hours. The solvent is then removed by rotary evaporator. The residue is dispersed in 50 mL CH₃OH, and 0.022 mol hydroxylamine hydrochloride and 0.06 mol trimethyl orthoformate are added. The reaction mixture is heated to reflux for 1 hour. The solvent is removed by rotary evaporator. Addition of water to the residue results in precipitation of N-[4-(1-hydroxyiminoethyl)phenyl]-N'-(1-methoxycarbonylethyl)urea, which is then treated with NaOCH₃ to adjust the pH to 10. The solution is heated to reflux for 2.5 hours, and the solvent is removed under vacuum. The residue is washed with cold water to yield the crude 3-[4-(1-hydroxyiminoethyl)phenyl]-≡-methylhydantoin. The hydantoin is purified by recrystallization from CH₃OH:H₂O.

EXAMPLE 38

A solution of 0.02 mol 4-aminoacetophenone in 40 mL THF if added dropwise to a solution of 0.02 mol of dimethyl isocyanatomalonate and 5 mL pyridine in 40 mL THF, and the reaction mixture is stirred for 3 hours. The solvent is then removed by rotary evaporator. The residue is dispersed in 50 mL CH₃OH, and 0.022 hydroxylamine hydrochloride and 0.06 mol trimethyl orthoformate are added. The reaction mixture is heated to reflux for 10 hours. The solvent is removed by rotary evaporator. Addition of water to the residue results in formation of N-[4-(1-hydroxyiminoethyl)phenyl]-N'-bis(methoxycarbonyl)methylurea, which is then treated with NaOCH₃ to adjust the pH to 10. The solution is heated to reflux for 2.5 hours, and the solvent is removed under vacuum. The residue is washed with cold water to yield the crude 3-[4-(1-hydroxyiminoethyl)phenyl]-5-methoxycarbonylhydantoin.

As will be evident to those skilled in the art, various modifications of this invention can be made or followed in the light of the foregoing disclosure and discussion without departing from the spirit and scope of the disclosure or from the scope of the claims.

We claim:
1. A compound of the formula

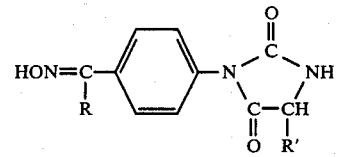

where each of R and R' has zero to 10 C atoms and no ethylenic or acetylenic unsaturation; R is H or hydrocarbyl; R' is H, hydrocarbyl, or hydrocarbyl substituted with hydrocarbylcarbonylamino, di(hydrocarbylcarbonyl)amino, hydrocarbylcarbonyl(hydrocarbyl)amino, formylamino, diformylamino and formyl(hydrocarbyl)amino, hydrocarbyloxy, hydrocarbylthio, formylthio, hydrocarbylcarbonylthio, hydrocarbyloxycarbonyl, hydrocarbyl carboxyl, hydrocarbylamino, dihyrocarbylamino, formyl, 3-indolyl, 3-(1-hydrocarbyl)indolyl, 3-(1-hydrocarbylcarbonyl)indolyl, 3-(1-formyl)indolyl, carbamoyl, hydrocarbylcarbamoyl, dihydrocarbylcarbamoyl, 5-imidazolyl, 5-(3-hydrocarbyl)imidazolyl, 5-(3-hydrocarbylcarbonyl)imidazolyl, or 5-(3-formyl)imidazolyl.

2. A compound of the formula

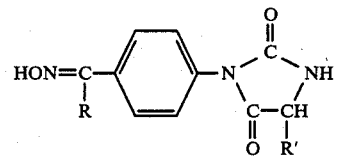

where each of R and R' has no ethylenic or acetylenic unsaturation; R has zero to 6 C atoms and is H or hydrocarbyl; R' has zero to 10 C atoms and is H, hydrocarbyl, or hydrocarbyl substituted with hydrocarbylcarbonylamino, di(hydrocarbylcarbonyl)amino, hydrocarbylcarbonyl(hydrocarbyl)amino, formylamino, diformylamino and formyl(hydrocarbyl)amino, hydrocarbyloxy, hydrocarbylthio, formylthio, hydrocarbylcarbonylthio, hydrocarbyloxycarbonyl, hydrocarbyl carboxyl, hydrocarbylamino, dihydrocarbylamino, formyl, 3-indolyl, 3-(1-hydrocarbyl)indolyl, 3-(1-hydrocarbylcarbonyl)indolyl, 3-(1-formyl)indolyl, carbamoyl, hydrocarbylcarbamoyl, dihydrocarbylcarbamoyl, 5-imidazolyl, 5-(3-hydrocarbyl)imidazolyl, 5-(3-hydrocarbylcarbonyl)imidazolyl, or 5-(3-formyl)imidazolyl.

* * * * *